United States Patent
Jin et al.

(10) Patent No.: US 10,542,916 B2
(45) Date of Patent: Jan. 28, 2020

(54) METHOD AND APPARATUS FOR TRACKING HAND AND/OR WRIST ROTATION OF A USER PERFORMING EXERCISE

(71) Applicant: KONINKLIJKE PHILIPS N.V., Eindhoven (NL)

(72) Inventors: Sheng Jin, Shanghai (CN); Yusi Liu, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1553 days.

(21) Appl. No.: 14/369,853

(22) PCT Filed: Dec. 28, 2012

(86) PCT No.: PCT/IB2012/057795
§ 371 (c)(1),
(2) Date: Jun. 30, 2014

(87) PCT Pub. No.: WO2013/098791
PCT Pub. Date: Jul. 4, 2013

(65) Prior Publication Data
US 2014/0371634 A1    Dec. 18, 2014

(30) Foreign Application Priority Data
Dec. 30, 2011 (WO) ............... PCT/CN2011/085060

(51) Int. Cl.
*A61B 5/11* (2006.01)

(52) U.S. Cl.
CPC .......... *A61B 5/1127* (2013.01); *A61B 5/1121* (2013.01); *A61B 5/1128* (2013.01)

(58) Field of Classification Search
None
See application file for complete search history.

(56) References Cited

U.S. PATENT DOCUMENTS

| 8,277,396 B2 | 10/2012 | Scott et al. |
| 2005/0213076 A1 | 9/2005 | Hiroshi |

(Continued)

FOREIGN PATENT DOCUMENTS

| CN | 104023634 A | 9/2014 |
| EP | 1970104 A1 | 9/2008 |

(Continued)

OTHER PUBLICATIONS

P. Cerveri et al., Finger Kinematic Modeling and Real-Time Hand Motion Estimation, Aug. 15, 2007, vol. 35, No. 11, pp. 1989-2002.*

(Continued)

*Primary Examiner* — Sean P Dougherty
*Assistant Examiner* — Benjamin S Melhus

(57) ABSTRACT

The present invention provides a method and apparatus for tracking hand and/or wrist rotation of a user performing exercise. An aspect of the present invention proposes a method of tracking hand and/or wrist rotation of a user performing an exercise, wherein the user wears a marker on his/her hand, the method comprising the steps of: acquiring a first image and a second image of the marker by means of a camera when the hand is in a first posture and a second posture respectively; deriving the angle change of the hand and/or wrist from the change from the first posture to the second posture, based on the first image and the second image and the type of the exercise that the user is performing; and outputting the angle change of the hand and/or wrist, wherein the marker approximates a rectangular block, the marker has an opening for accommodating the palm(s) of the user and the side of the marker along the direction perpendicular to the palm is substantially shorter than two other sides. In this way, a single hand-worn marker is adequate for hand/wrist rotation tracking, so that the system (Continued)

implementation may be simplified and the cost for markers or other accelerometers can be saved.

10 Claims, 7 Drawing Sheets

(56) References Cited

U.S. PATENT DOCUMENTS

| | | | |
|---|---|---|---|
| 2006/0129070 A1* | 6/2006 | Pearl | A61B 5/0057 600/595 |
| 2007/0207873 A1 | 9/2007 | Rose | |
| 2008/0036737 A1 | 2/2008 | Hernandez-Rebollar | |
| 2009/0131225 A1 | 5/2009 | Burdea et al. | |
| 2009/0231278 A1 | 9/2009 | Hilaire et al. | |
| 2010/0251763 A1 | 10/2010 | Audun | |
| 2014/0371634 A1 | 12/2014 | Jin et al. | |

FOREIGN PATENT DOCUMENTS

| | | |
|---|---|---|
| JP | 2001133300 A | 5/2001 |
| JP | 201192274 A | 5/2011 |
| WO | 2008099301 A1 | 8/2008 |
| WO | 2010022882 A2 | 3/2010 |
| WO | 2011113070 A1 | 9/2011 |

OTHER PUBLICATIONS

Smart-DX Webpage; http://www.btsbioengineering.com/products/smart-dx/.*

Durgin, F , Palm boards are not action measures: an alternative to the two-systems theory:, Acta Psychologica V 134, N2, Jun. 1, 2010, p. 182-197.

Durgin, F.H. et al. "Palm boards are not action measures: An alternative to the two-systems theory of geographical slant perception", ACTA Psychologica, North Holland, Amsterdam, N>, vol. 134, No. 2, Jun. 1, 2010, pp. 182-197.

Kofman, J. et al: "Teleoperation of a Robot Manipulator Using a Vision-Based Human Robot Interface", IEEE Transactions on Industrial Electronics, ICCC Service Center, Piscataway, NJ, vol. 52, No. 5, Oct. 1, 2005, pp. 1206-1219.

Cerven, P. et al. "Finger Kinematic Modeling and Real-Time Hand Motion Estimation", Annals of Biomedical Engineering, Kluwer Academic Publishers-Plenum Publishers, NE, vol. 35, No. 11, Aug. 15, 2007, pp. 1989-2002.

* cited by examiner

METHOD AND APPARATUS FOR TRACKING HAND AND/OR WRIST ROTATION OF A USER PERFORMING EXERCISE

This application is a national stage application under 35 U.S.C. § 371 of International Application No. PCT/IB2012/057795 filed on Dec. 28, 2012 and published in the English language on Jul. 4, 2013 as International Publication No. WO/2013/098791, which claims priority to International Application No. PCT/CN2011/085060 filed on Dec. 30, 2011, the entire disclosures of which are incorporated herein by reference.

FIELD OF THE INVENTION

The invention relates to hand and/or wrist rotation tracking, and particularly to a method and an apparatus for tracking hand and/or wrist rotation of a user performing exercise.

BACKGROUND OF THE INVENTION

A single video-camera and marker-based stroke rehabilitation system is a cost effective solution for emerging markets. With a TV set, post-stroke patients can do rehabilitation exercises by themselves according to the guidance on the screen prescribed by doctors/therapists.

WO2008/099301A1 discloses a feedback device for guiding and supervising physical exercises. Although it utilizes body-worn sensors or markers and a camera system to detect a body posture and/or body movement of the person, the feedback device can only detect the body posture as a whole and cannot accurately detect the angle change in a rotation exercise of, for example, hand and/or wrist.

Specifically, of all rehabilitation exercises, hand and/or wrist related rotation movements are important exercises for post-stroke patients. In the case of a hand-worn marker of arbitrary shape like an ellipsoid ball or a cube, it is difficult for a single camera-based system to track 3 degrees of freedom of hand rotation. In most cases, in order to complete this task, additional markers on the hand, or other modalities like accelerometers, have to be used to help to track rotation.

SUMMARY OF THE INVENTION

In order to simplify the system implementation and reduce the number of markers for hand and/or wrist rotation tracking, the inventors of the present invention carefully studied all kinds of hand/wrist rotation-related exercises and found that these exercises may be classified into two categories: i.e., the first category, which does not relate to the area change of the image of the marker acquired by the camera (for example, the hand/wrist rotation along with forearm pronation and supination); and the second category, which relates to the area change of the image of the marker acquired by the camera (for example, the wrist dorsiflexion and palmar flexion).

Further, the inventors realize that hand and/or wrist rotation tracking for exercises belonging to the first category may be implemented by a line-fitting algorithm, and hand/wrist rotation tracking for exercises belonging to the second category may be implemented by an area-angle mapping algorithm.

Nevertheless, not all markers of arbitrary shape could be used for these two algorithms. In other words, the two algorithms should be used in conjunction with a specifically designed hand-worn marker to make these two algorithms feasible at the same time. In this way, a single hand-worn marker is adequate for hand and/or wrist rotation tracking, so that the system implementation may be simplified and the cost for markers or other accelerometers can be saved.

As mentioned above, the inventors of the present invention have found that the shape of the hand-worn marker cannot be arbitrary, especially for a line-fitting algorithm. For example, if the projection of the marker to the camera is a circular shape or a square shape, the image acquired by the camera cannot be line-fitted into a line, and therefore the hand/wrist rotation represented by the maker movement cannot be identified by a line-fitting algorithm.

Therefore, in view of the above, the inventors have found that in order to make hand and/or wrist rotation tracking suitable for both area-angle mapping algorithms and line-fitting algorithms at the same time with a single marker, the projection of the marker to the camera should be rectangle-like in shape, and preferably have a slim rectangle shape to be suitable for line-fitting. In other words, the projection of the marker should not be of circular shape or square shape, etc.

Specifically, according to one aspect of the present invention, there is provided a method of tracking hand and/or wrist rotation of a user performing an exercise, wherein the user wears a marker on his/her hand, the method comprising the steps of:

acquiring a first image and a second image of the marker by a camera when the hand is in a first posture and a second posture, respectively;

deriving the angle change of the hand and/or wrist from the change from the first posture to the second posture, based on the first image and the second image and the type of the exercise that the user is performing; and outputting the angle change of the hand and/or wrist, wherein the marker approximates a rectangular block, the marker has an opening for accommodating the palm(s) of the user and the side of the marker along the direction perpendicular to the palm is substantially shorter than two other sides.

Since the side of the marker along the direction perpendicular to the palm is substantially shorter than two other sides, the projection thereof to the camera is rectangular in shape and can be line-fitted into a line. Accordingly, the hand-worn marker with the shape mentioned above is suitable for line-fitting algorithms. Therefore, with the method of the present invention, a single hand-worn marker is adequate for hand and/or wrist rotation tracking, so that the system implementation may be simplified and the cost for marker or other accelerometers can be saved.

According to an embodiment of the present invention, when the type of the exercise the user is performing relates to forearm supination and pronation and the first and second image are elongate, the deriving step comprises the sub-steps of:

fitting the first and second image into a first and second line respectively; and calculating the angle between the first and second line as the angle change of the hand and/or wrist.

In this way, as mentioned above, hand and/or wrist rotation tracking for this type of exercise may be easily performed by utilizing the line-fitting algorithm in conjunction with the simple hand-worn marker.

Further, according to an embodiment of the present invention, when the type of exercise the user is performing relates to wrist dorsiflexion and palmar flexion, the deriving step comprises the sub-steps of:

calculating the first and second area of the first and second image respectively;

mapping the first area to a first angle by looking up a predefined table, the first angle indicating the angle of the plane the marker lies on when the marker is at the first posture relative to a reference plane;

mapping the second area to a second angle by looking up the predefined table, the second angle indicating the angle of the plane the marker lies on when the marker is at the second posture relative to the reference plane; and calculating the angle difference between the first and the second angle as the angle change of the hand and/or wrist.

In this way, as mentioned above, hand and/or wrist rotation tracking for this type of exercise may be easily performed by utilizing the area-mapping algorithm in conjunction with the simple hand-worn marker.

As for how to establish the predefined table, in accordance with a preferred embodiment of the present invention, in order to distinguish two images which have the same area but correspond to different postures (for example, two images having the same area but acquired during wrist flexion and extension, respectively), it is an option to take the plane of the marker, at which the area of the acquired image of the marker is at a minimum, as the reference plane and refer to the center of the marker to distinguish the signs for different postures corresponding to the same area of the acquired image.

According to another aspect of the present invention, there is provided an apparatus for tracking hand and/or wrist rotation of a user performing exercise, wherein the user wears a marker on his/her hand, the apparatus comprising:

a camera configured to acquire a first image and a second image of the marker when the hand is in a first posture and a second posture respectively;

a processor configured to derive the angle change of the hand and/or wrist from the change from the first posture to the second posture, based on the first image and the second image and the type of exercise that the user is performing; and an interface configured to output the angle change of the hand and/or wrist, wherein the marker approximates a rectangular block, the marker has an opening for accommodating the palm(s) of the user and the side of the marker along the direction perpendicular to the palm is substantially shorter than two other sides.

As mentioned above, since the hand-worn marker with the shape mentioned above is suitable for line-fitting algorithms, by utilizing the apparatus of the present invention, a single hand-worn marker is adequate for hand and/or wrist rotation tracking, so that the system implementation may be simplified and the cost for marker or other accelerometers can be saved.

According to a further embodiment of the present invention, the processor is further configured to generate instruction information based on the angle change and the set-up goal of the exercise and the interface is further configured to provide the instruction information to the user by video and/or audio.

In this way, the apparatus may provide real-time feedback which is basically a display of the result of the detection or a voice prompt, which is shown or provided in an understandable way to the user. Accordingly, the experience of the user is improved.

According to an embodiment of the present invention, the marker has three sides a, b, and c that correspond to respectively the thickness, length, and width of the palm when the user puts his/her palm(s) into the opening. In a preferred embodiment, the sizes for a, b and c are: a=55 mm~75 mm, b=195 mm~220 mm, c=155 mm~170 mm to fit the shape of a human's hand, so that the marker is more comfortable and more convenient for the user.

As for the type of the marker and the camera to be used in the present invention, the combination of retro-reflective marker and infra-red camera may be preferred. The advantage of using a retro-reflective marker is that a very high contrast in comparison with non-reflective areas can be achieved, so it is beneficial for image segmentation. By putting the markers at certain positions of a patient like upper limb joints, the arm movement can be tracked.

Nevertheless, the implementation of the present invention is not restricted to the combination of "retro-reflective marker and infra-red camera", but can be used in other "marker plus camera"-based configurations.

For example, the marker may not necessarily be a retro-reflective marker, but can be simply an ordinary marker in red color or any other color distinguishable from the surrounding environment of the marker. In this case, the camera may be an ordinary camera if the algorithm used therein can segment image elements by color recognition. In other words, other types of marker and camera may be utilized, as long as the image of the marker acquired by a camera can be distinguished from the image of the surroundings.

Other objects and advantages of the present invention will become more apparent from, and will be easily understood with reference to, the description made in combination with the accompanying drawings.

DESCRIPTION OF THE DRAWINGS

The present invention will be described and explained hereinafter in more detail in combination with embodiments and with reference to the drawings, in which.

The same reference signs in the figures indicate similar or corresponding features and/or functionalities.

DETAILED DESCRIPTION

An embodiment of the present invention will be described hereinafter in more detail with reference to the drawings.

The hand-worn marker should not only be fit to be worn by post-stroke patients, but should also technically support rotation tracking on 3 degrees of freedom. It is hard for stroke patients to wear the glove with a separate sheath design, therefore, the basic shape should be designed as a fingerless glove.

Figure 1A:
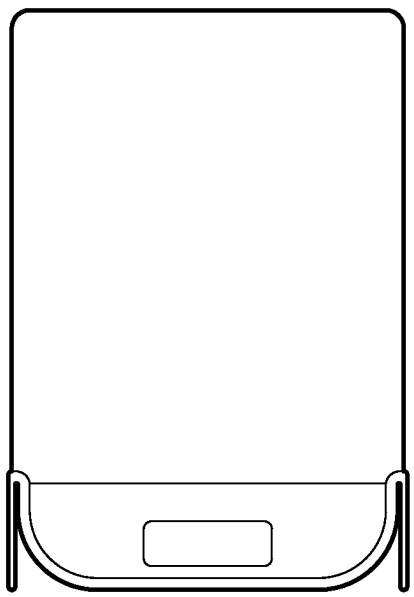
FIGS. 1$a$-1$c$ show a top view, front view and side view, respectively, of the hand-worn marker.
Figure 1B:
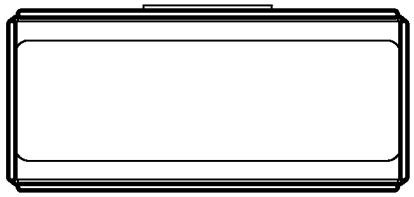
Figure 1C:
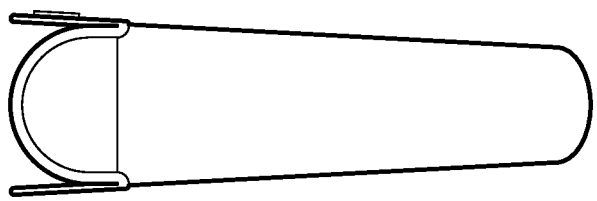

FIGS. 1a-1c show the top view, front view and side view, respectively, of the hand-worn marker. The retro-reflective materials are pasted on the outside of the glove (i.e., the hand-worn marker) to reflect infra-red lights.

Figure 2:
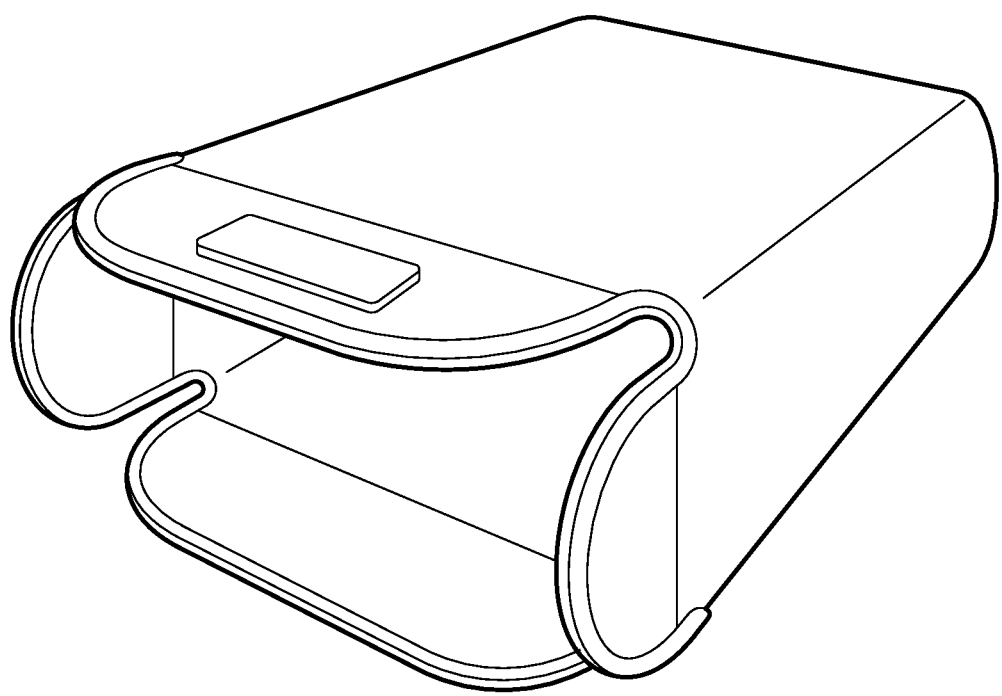
FIG. 2 shows a perspective view of the hand-worn marker.

FIG. 2 further shows a perspective view of the hand-worn marker. As can be seen from FIG. 2, the glove has a flip-over design, specifically helping the user with dysfunction of one side of the limbs put it on more conveniently.

Figure 3:
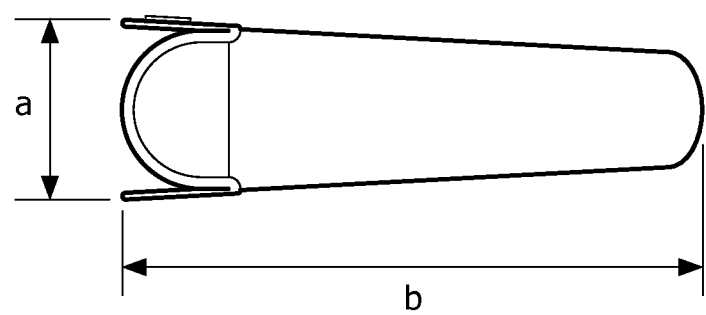
FIG. 3 shows the geometry of the hand-worn marker in accordance with an embodiment of the present invention.
Figure 3:
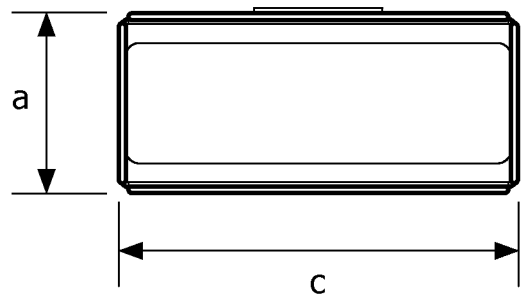

FIG. 3 shows the geometry of the hand-worn marker in accordance with an embodiment of the present invention.

As can be seen from FIG. 3, the shape of the marker is substantially a rectangular box. The marker has three sides a, b, and c that correspond to, respectively, the thickness, length, and width of the palm when the user puts his/her palm(s) into the opening.

According to the present invention, at least one of a, b and c is unequal to the other two, so that at least a pair of side surfaces of the six side surfaces constituting the box are rectangles and are capable of being line-fitted into a line.

The marker has an opening for accommodating the palm (s) of the user and the side of the marker along the direction perpendicular to the palm is substantially shorter than two other sides.

The side of the marker along the direction perpendicular to the palm is substantially shorter than two other sides, and the projection to the camera is rectangular in shape, which can be line-fitted into a line along the direction parallel to the palm. Accordingly, the hand-worn marker with the shape mentioned above is suitable for line-fitting algorithms.

According to an embodiment of the present invention, to make the marker suitable for the shape of a human hand, it is preferable that $b>c>a$.

Further, to improve the wearability for the user, a is preferably selected to be in the range of 55 mm~75 mm, b is preferably selected to be in the range of 195 mm~220 mm, and c is preferably selected to be in the range of 155 mm~170 mm.

It is further preferable to select these parameters in accordance with the sex of the user so as to take into account the hand's shape for male or female users.

For example, for adult male users, a=60 mm~75 mm, b=205 mm~220 mm, c=160 mm ~170 mm; and for adult female users, a=55 mm~65 mm, b=195 mm~210 mm, and c=155 mm~165 mm.

In a preferred embodiment of the present invention, a may be selected to be 63 mm, b may be selected to be 210 mm, and c may be selected to be 165 mm.

As mentioned above, the inventors of the present invention have found that these hand and/or wrist rotation-related exercises may be classified into two categories: the first of which does not relate to the area change of the image of the marker acquired by the camera (for example, the hand/wrist rotation along with forearm pronation and supination); and the second of which relates to the area change of the image of the marker acquired by the camera (for example, wrist dorsiflexion and palmar flexion).

Further, the inventors have realized that hand and/or wrist rotation tracking for exercises belonging to the first category may be implemented by line-fitting algorithms, and hand and/or wrist rotation tracking for exercises belonging to the second category may be implemented by area-angle mapping algorithms.

In the following, the hand and/or wrist rotation along with forearm pronation and supination is illustrated as an example of exercises in the first category with reference to FIGS. 4 and 5.

Figure 4:
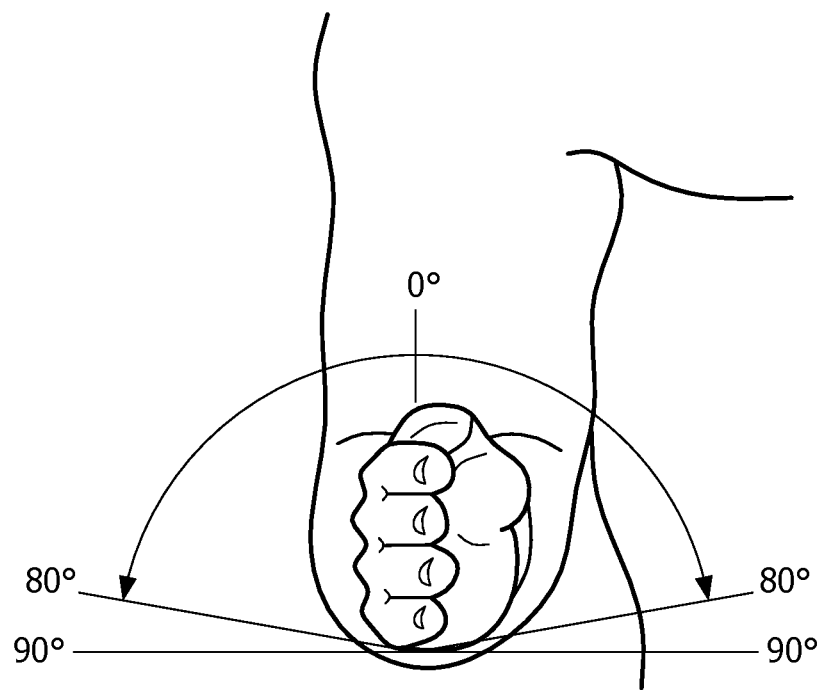
FIG. 4 is an illustrative view showing the definition of initial posture of the hand during forearm pronation and supination.

FIG. 4 is an illustrative view showing the definition of initial posture of the hand during forearm pronation and supination.

As can be seen from FIG. 4, the posture in which the hand is perpendicular to the horizontal plane (i.e., 0° position of the hand shown in FIG. 4) may be selected as the initial posture of the hand for forearm pronation and supination exercise.

Figure 5:
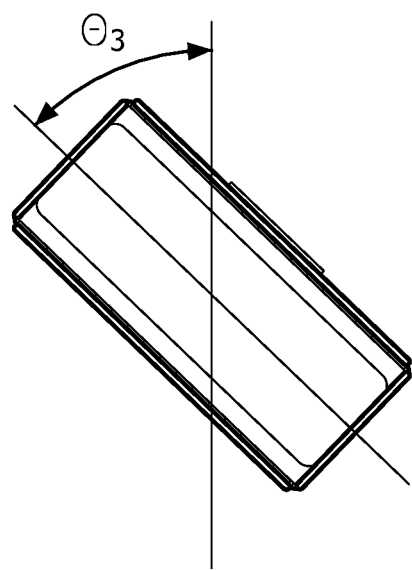
FIG. 5 is an illustrative view showing the angle change of the hand and/or wrist obtained by utilizing the line-fitting algorithm.

FIG. 5 is an illustrative view showing the angle change of the hand and/or wrist obtained by utilizing the line-fitting algorithm.

In accordance with the line-fitting algorithm, when the marker is worn on the hand and imaged by the camera, the first and second image are elongate and all the pixels of the image of the marker will be fitted into a line along the length direction of the image.

If the image of the marker acquired when the hand is in the first posture is fitted into the first line, and the image of the marker acquired when the hand is in the second posture is fitted into the second line, then the angle between the first line and the second line can be calculated as the angle change of the hand and/or wrist.

Please note that although the first posture in the present embodiment is the same as the initial posture, the first posture may also deviate from the initial posture. For example, the first posture may not be the 0° position of the hand shown in FIG. 4, but can be an 80° position of the hand shown in the left of FIG. 4.

In the following, the wrist dorsiflexion and palmar flexion is illustrated as an example of exercise in the second category with reference to FIG. 6.

Figure 6:
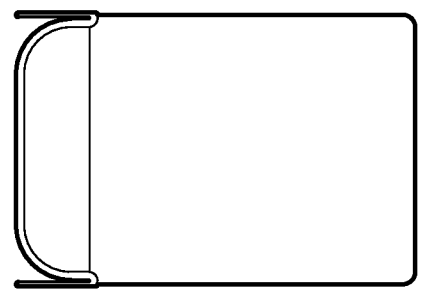
FIG. 6 is an illustrative view showing the area changes of the hand-worn marker in the front view during wrist flexion and extension.
Figure 6:
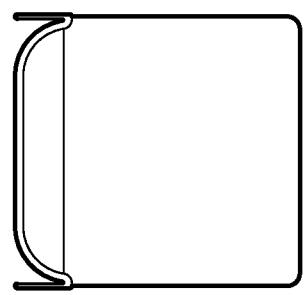
Figure 6:
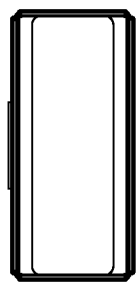
Figure 6:
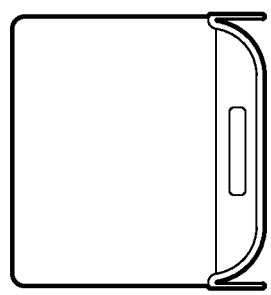
Figure 6:
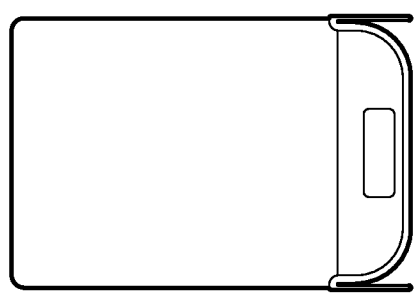

FIG. 6 is an illustrative view showing the area changes of the hand-worn marker in a front view during wrist dorsiflexion and palmar flexion.

As can be seen from FIG. 6, the area of the marker changes due to different wrist flexion and extension angle. The hand-worn marker is designed to have a certain shape when the user performs wrist dorsiflexion and palmar flexion in the transverse plane. If a minimum area of the image of the marker representing a natural position of the wrist and the plane of the marker, at which the area of the image of the marker is at a minimum, is taken as the reference plane (0° position), the maximum area of the image of the marker will represent a 90° flexion or extension of the wrist.

In order to distinguish the extension or flexion of the wrist, the center of the marker may be tracked and compared to its original position when the wrist is in the natural position. The center position of the marker in the case of flexion exercises should be opposite to the position in the case of extension exercises.

In this regard, as can be readily understood by those skilled in the art, the center position of the marker is just an example of the way of distinguishing extension and flexion, while other positions in the glove or other references could be adopted as long as they can be used for this purpose.

Figure 7:
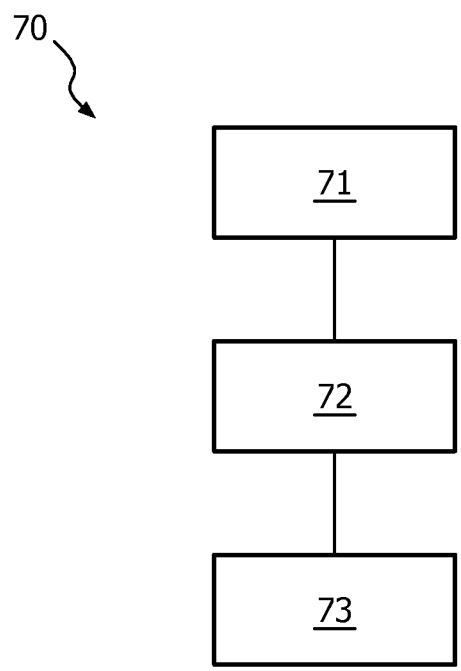
FIG. 7 is a flowchart of the method of tracking hand and/or wrist rotation of a user performing exercise in accordance with an embodiment of the present invention.

FIG. 7 is a flowchart of the method of tracking hand/wrist rotation of a user performing an exercise in accordance with an embodiment of the present invention.

As shown in FIG. 7, a method 70 of tracking hand/wrist rotation of a user performing an exercise is proposed.

Specifically, this method 70 is used in conjunction with the above-mentioned hand-worn marker and comprises an acquiring step 71, a deriving step 72 and an outputting step 73.

At first, a first image and a second image of the marker, when the hand is in a first posture and a second posture respectively, are acquired by a camera (step 71).

Then, the angle change of the hand and/or wrist associated with the change from the first posture to the second posture is derived based on the first image and the second image and the type of exercise that the user is performing (step 72).

The algorithm to be used is selected in accordance with the type of exercise that the user is performing. For example, the angle change of the hand and/or wrist is derived by using a line-fitting algorithm when the type of exercise the user is performing relates to forearm supination and pronation and the first and second image are elongate. Further, the angle change of the hand and/or wrist is derived by using an area-angle mapping algorithm when the type of exercise the user is performing relates to wrist dorsiflexion and palmar flexion.

In accordance with an embodiment of the present invention, when the type of exercise the user is performing relates to forearm supination and pronation and the first and second image are elongate, the deriving step comprises the sub-steps of:
fitting the first and second image into a first and second line respectively; and
calculating the angle between the first and second line as the angle change of the hand and/or wrist.

Details of the line-fitting algorithm will be omitted here, since it has been described above in combination with FIGS. 4-5.

In accordance with an embodiment of the present invention, when the type of exercise the user is performing relates to wrist dorsiflexion and palmar flexion, the deriving step comprises the sub-steps of:
calculating the first and second area of the first and second image respectively;
mapping the first area to a first angle by looking up a predefined table, the first angle indicating the angle of the plane the marker lies on when the marker is at the first posture relative to a reference plane;
mapping the second area to a second angle by looking up the predefined table, the second angle indicating the angle of the plane the marker lies on when the marker is at the second posture relative to the reference plane; and
calculating the angle difference between the first and the second angle as the angle change of the hand and/or wrist.

As for how to establish the look-up table, in accordance with a preferred embodiment of the present invention, the plane of the marker, at which the area of the image of the marker is at a minimum, is taken as the reference plane (0° position). Accordingly, the posture, in which the area of the image of the marker is at a minimum, may be selected as the initial posture for the exercise.

Similarly to the case of line-fitting, although the first posture in the present embodiment may be the same as the initial posture, the first posture may also not be the same as the initial posture. In other words, the first posture may not be a 0° position (the position shown in the middle of FIG. 6), but can be any other position shown in FIG. 6.

In a further embodiment, in order to distinguish two postures at which the areas of the images of the marker are the same and the planes of the marker when the hand is in the two postures are located on two sides of the reference plane, it is an option to refer to the center of the marker to distinguish these two postures and assign two angles to them which are the same in magnitude but different in sign.

As mentioned above, it can be readily understood by those skilled in the art that referring to the center position of the marker is just an example of a way of distinguishing extension and flexion; other positions in the marker or other references could be adopted as long as they can be used for this purpose.

Once the angle change of the hand and/or wrist is obtained, it could be outputted to the user (step 73).

Although not shown in FIG. 7, in an embodiment of the present invention, the method of the present invention may further comprise the steps of: generating instruction information based on the angle change and the set-up goal of the exercise; and providing the instruction information to the user by video and/or audio.

For example, the angle change of the hand and/or wrist may be displayed in a real-time manner such that the set-up goal regarding angle-change for the exercise that the user is performing is displayed as a reference figure. In this way, a real-time feedback which is basically a display of the result of the detection can be provided in an understandable way to the user. Accordingly, the experience of the user is improved.

The above idea may be more easily understood by referring to FIG. 9. Specifically, FIG. 9 shows the angle change presentation in the real-time feedback on the display.

Figure 9A:
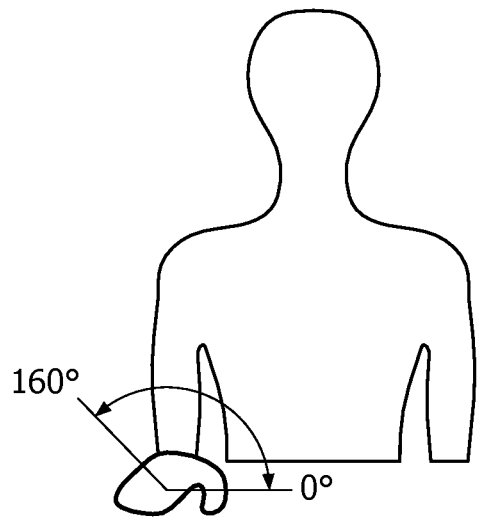
FIG. 9 shows the angle change presentation in real-time feedback on the display.
Figure 9B:
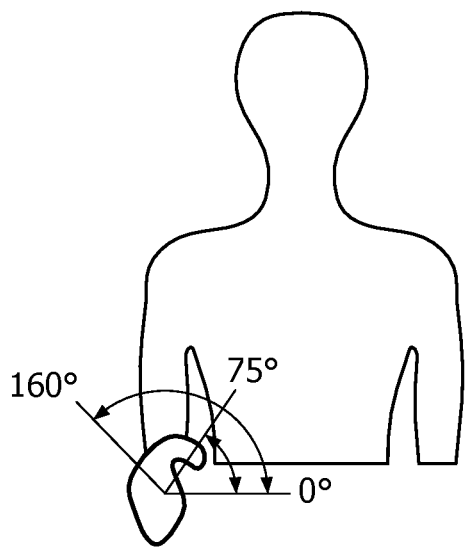
Figure 9C:
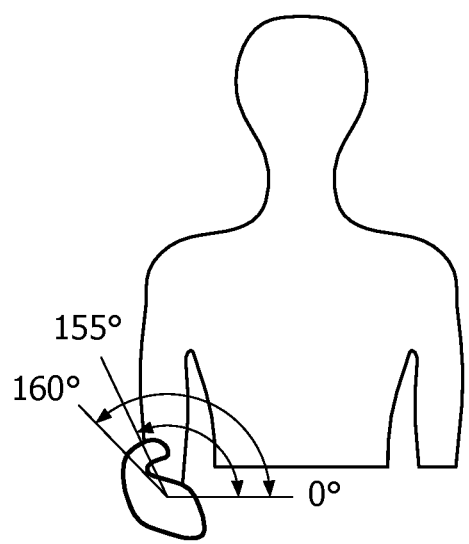

The set-up goal of each rotation exercise is displayed as a sector-shaped figure and the action line and rotated angle are displayed (FIG. 9a). When the user rotates his hand and/or wrist, the action line moves in alignment with the arc of the sector. And the rotated angle changes accordingly (FIGS. 9b and 9c).

Sometimes, when the rotation action is too subtle on the screen, the user may find it difficult to visually perceive the rotation. In this case, an enlarging function may be provided, which may magnify the rotation-related area so that the user can really see how well he is doing and how much he has rotated. To increase the user's understanding of the rotation exercises as well as motivate the user while he is doing the exercises, a cartoon character introduction can be placed beside the real-time feedback, telling the user how exactly he should perform and what key points he should observe about the current exercise.

Figure 8:
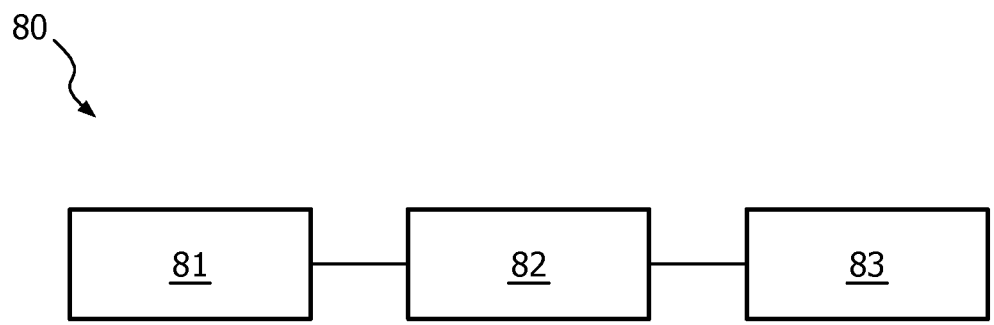
FIG. 8 is a block diagram of the apparatus for tracking hand and/or wrist rotation of a user performing exercise in accordance with an embodiment of the present invention.

FIG. 8 is a block diagram of the apparatus for tracking hand and/or wrist rotation of a user performing exercise in accordance with an embodiment of the present invention.

As can be seen from FIG. 8, an apparatus 80 for tracking hand and/or wrist rotation of a user performing exercise is proposed. Specifically, this apparatus 80 is used in conjunction with the above-mentioned hand-worn marker and comprises a camera 81, a processor 82 and an interface 83.

The camera 81 in FIG. 8 is used for acquiring a first image and a second image of the marker when the hand is in a first posture and a second posture, respectively.

After the images are acquired, the processor 82 is used for deriving the angle change of the hand and/or wrist from the change from the first posture to the second posture, based on the first image and the second image and the type of the exercise that the user is performing.

The interface 83 is configured for outputting the angle change of the hand and/or wrist to the user.

In an embodiment of the present invention, the interface 83 may be configured for visually displaying the angle change of the hand and/or wrist on a display or outputting the angle change by a speaker.

In this way, the apparatus may provide a real-time feedback which is basically a display of the result of the detection or a voice prompt, which is shown or provided in an understandable way to the user. Accordingly, the experience of the user is improved.

Please note that the description of the retro-reflective marker and the infra-red camera in the embodiment is only for illustrative purposes and should not be construed in a limiting sense. As mentioned above, the implementation of the present invention is not restricted to the combination with "retro-reflective marker and infra-red camera", but can be used in other "marker plus camera"-based configurations.

For example, the marker may not necessarily be the retro-reflective maker, but can be simply an ordinary marker in red color or any other color distinguishable from the surrounding environment of the hand. In this case, the camera may be an ordinary camera as long as the image of the marker acquired by a camera is capable of being distinguished from the image of the surroundings.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. In the system claims enumerating several units, several of these units can be embodied by one and the same item of software and/or hardware. The usage of the words first, second and third, et cetera, does not indicate any ordering. These words are to be interpreted as names.

The invention claimed is:

1. A method of tracking hand and/or wrist rotation of a user performing an exercise, wherein the user wears a marker on his/her hand, the method comprising:
   acquiring a first image and a second image of the marker by a camera when the hand is in a first posture and a second posture, respectively; deriving the angle change of the hand and/or wrist from the change from the first posture to the second posture,
   based on the first image and the second image and the type of the exercise that the user is performing, and generating instruction information based on the angle change and at least one set-up goal of the exercise;
   and outputting the instruction information to the user by video and/or audio,
   wherein the marker comprises a box having six sides and an interior volume within the six sides, wherein at least three of the six sides comprise surfaces that are detectable by the camera and at least one side comprises an opening that enables a palm of the user to be placed within the interior volume and the sides of the marker along the direction perpendicular to the palm are shorter than the other sides;
   and wherein the method derives the angle change based on characteristics of at least one of the surfaces appearing in the first and second images.

2. The method of claim 1, wherein, when the type of exercise the user is performing relates to forearm supination and pronation and the first and second image are elongate, the deriving step comprises:
   fitting the appearance of the at least one surface in the first and second image into a first and second line, respectively; and
   calculating an angle between the first and second line as the angle change of the hand and/or wrist.

3. The method of claim 1, wherein, when the type of exercise the user is performing relates to wrist dorsiflexion and palmar flexion, the deriving step comprises:
   calculating a first and second area of the appearance of the at least one surface in the first and second image, respectively;
   mapping the first area to a first angle by looking up a predefined table that defines a relationship between area values and angle values, the first angle indicating the angle of the plane the marker lies on when the marker is at the first posture relative to a reference plane;
   mapping the second area to a second angle by looking up the predefined table, the second angle indicating the angle of the plane the marker lies on when the marker is at the second posture relative to the reference plane; and
   calculating the angle difference between the first and the second angle as the angle change of the hand and/or wrist.

4. The method of claim 3, wherein the reference plane is defined as a plane at which a projection of the at least one surface in the camera has a minimum area.

5. Apparatus for tracking hand and/or wrist rotation of a user performing an exercise, the apparatus comprising:
   a marker to be worn on a hand of the user;
   a camera configured to acquire a first image and a second image of the marker when the hand is in a first posture and a second posture, respectively;
   a processor configured to: derive an angle change of the hand and/or wrist from the change from the first posture to the second posture, based on the first image and the second image and a type of the exercise that the user is performing, and generate instruction information based on the angle change and at least one set-up goal of the exercise;
   and an interface circuit configured to provide the instruction information to the user by video and/or audio,
   wherein the marker comprises a box having six sides and an interior volume within the six sides, wherein at least three of the six sides comprise surfaces that are detectable by the camera, and at least one side comprises an opening that enables a palm of the user to be placed within the interior volume and the sides of the marker along a direction perpendicular to the palm are shorter than the other sides;
   and wherein the processor determines the angle change based on characteristics of at least one of the surfaces appearing in the first and second images.

6. The apparatus of claim 5, wherein, when the type of the exercise that the user is performing relates to forearm supination and pronation, the processor:
   fits the appearance of the at least one surface in the first and second image into a first and second line, respectively; and
   calculates an angle between the first and second line as the angle change of the hand and/or wrist.

7. The apparatus of claim 5, wherein, when the type of exercise the user is performing relates to wrist dorsiflexion and palmar flexion, the processor:
   calculates a first and second area of the at least one surface in the first and second image, respectively;

maps the first area to a first angle by looking up a predefined table that defines a relationship between area values and angle values, the first angle indicating the angle of the plane the marker lies on when the marker is at the first posture relative to a reference plane;

maps the second area to a second angle by looking up the predefined table, the second angle indicating the angle of the plane the marker lies on when the marker is at the second posture relative to the reference plane; and calculates the angle difference between the first and the second angle as the angle change of the hand and/or wrist.

8. The apparatus of claim 7, wherein the reference plane is defined as a plane at which a projection of the at least one surface in the camera has a minimum area.

9. The apparatus of claim 5, wherein the camera is an infra-red camera and the at least three surfaces of the marker are coated with retro-reflective material that is capable of being imaged by the infra-red camera.

10. The apparatus of claim 9, wherein the marker has three dimensions a, b, and c that correspond to, respectively, a thickness, length, and width of the marker, and wherein 'a' ranges from 55 mm to 75 mm; 'b' ranges from 195 mm to 220 mm; and 'c' ranges from 155 mm to 170 mm.

* * * * *